United States Patent
Murad et al.

(12)

(10) Patent No.: US 6,187,333 B1
(45) Date of Patent: Feb. 13, 2001

(54) METHOD FOR TREATING, CONTROLLING, AND PREVENTING DIABETES MELLITUS

(75) Inventors: Osama Mansour Murad; Husni Abu Seir; Hafez Taji Farouqi, all of Amman (JO)

(73) Assignee: Diabex, Inc., Wake Forest, NC (US)

( * ) Notice: Under 35 U.S.C. 154(b), the term of this patent shall be extended for 0 days.

(21) Appl. No.: 09/399,616

(22) Filed: Sep. 20, 1999

(51) Int. Cl.$^7$ ........................................... A61K 9/02
(52) U.S. Cl. .................. 424/436; 424/451; 424/463; 424/464; 424/422; 514/552; 514/11; 514/783
(58) Field of Search .................... 424/451, 463, 424/464, 422, 436; 514/552, 11, 866, 783

(56) References Cited

U.S. PATENT DOCUMENTS

| | | | |
|---|---|---|---|
| 5,206,219 | * 4/1993 | Desai | 514/3 |
| 5,260,313 | * 11/1993 | Frome | 514/552 |
| 5,665,386 | * 9/1997 | Benet et al. | 424/451 |
| 5,972,382 | * 10/1999 | Majeed et al. | 424/464 |

FOREIGN PATENT DOCUMENTS

405043454 * 2/1993 (JP) .

OTHER PUBLICATIONS

Afifi, F.U., Saket, M. and jaghabir, M. 1998. Hypoglycemic effect of linalool in normal and streptozotocin diabetic rats. Acta Technol. and Leg. Med. vol. IX, N.2, pp. 101–106.*

* cited by examiner

Primary Examiner—Thurman K. Page
Assistant Examiner—Liliana Di Nola-Baron
(74) Attorney, Agent, or Firm—Ladas & Parry

(57) ABSTRACT

This invention pertains to a method that can control, treat, and prevent Diabetes Mellitus. The method includes means of administering a potent product, including mainly the active ingredient Linalool, in any one of several forms, alone or with other additives and catalysts, such as vitamin E to enable the body to handle and control, then correct the complications of Diabetes Mellitus. A modest percentage of users suffering from this disease can be cured completely while the majority of others improve remarkably and experience lower blood glucose and reduce the glycated hemoglobin HbAlc readings to what are medically acceptable and healthy levels. Others, who are vulnerable to the disease due to hereditary factors, or other reasons, can help prevent it. The method works in several ways, including activation of the pancreas and re-establishing the ability of body cells to utilize and handle better and well, the glucose in the blood, and regulate the level of natural insulin in the body. The method employs Linalool in any one of its forms that can be found naturally or synthetically.

14 Claims, No Drawings

METHOD FOR TREATING, CONTROLLING, AND PREVENTING DIABETES MELLITUS

FIELD OF THE INVENTION

This invention relates to a method that can be used to treat, control, cure, and prevent Diabetes Mellitus, of all types, through the administration of Linalool, alone, in any form, and possibly with other hypoglycemic additives in several forms, and by various means. The method does not cause any harmful or unpleasant side effects.

BACKGROUND OF THE INVENTION

Diabetes Mellitus is a feared and complex disorder. It has been a most distressing disease that can develop to a seriously life threatening condition. For ages, society was resigned to accepting various methods and medications that became a standard with no real hope for a cure, or drastic eradication of the disease. In fact, many of the drugs used cause serious side effects.

A most important indicator of the ability of the body to deal with the complications of diabetes is the glycated hemoglobin HbAlc, that gives an integrated reading of the level of blood glucose. While all other known methods and medications help lower the glucose level at limited periods of the day or night time, the HbAlC remains higher than the normal 4.3 to 6.7 range regardless of the insulin dosage and other medicines. No full cure is expected or hoped for by the present regimens. The described method herein is new and unique, and actually reduces the HbAlc reading to the normal levels and for all patients. This method has actually cured some patients of both types I and II diabetes to such a degree that they stopped taking any medication while leading normal lives.

The knowledge gained by the inventors through years of research, testing, and development work on tens of ancient folk herbs and methods, gave an incentive to aim to identify active beneficial components and ingredients, in dealing with various diseases. The result of the work of the inventors indicated that Pelargonium Graveolens contains substances that are beneficial and helpful in treating several diabetic complications. Our continuing studies and experiments on animals, mice, rats, and rabbits, and later tests on human volunteers, enabled the inventors to identify and effectively employ Linalool for treating and preventing, and in some cases, curing Diabetes Mellitus.

Numerous tests were conducted on various types of animals using:

Water extract of Pelargonium Graveolens plant.

Crude oil of the extract of the plant (Geranium Oil) which contains mainly Linalool, Geraniol, Citronellol, Eugenol.

Linalool oil

Each of the components above was tested alone, and in combination with other substances, such as Vitamin E, and observations were made regarding contribution to hypoglycemic effects. It became ultimately evident and clear to us, that Linalool is a potent, effective, and active hypoglycemic ingredient.

Linalool can be obtained naturally from the labiate family plants, or could be chemically synthesized, maintaining the same hypoglycemic effect. Our further work and tests led us to perfect a method for utilizing Linalool in several forms for curing, treatment, control, and prevention of Diabetes Mellitus.

PRIOR ART

The present invention has not been found in prior art, nor does prior art suggest or teach anything resembling this invention. The search regarding the usage of Linalool in all available electronic and published literature, led us to the followings:

Linalool, Cironnellol, and Eugenol have been found to have many pharmacological activities and as listed below:

Pet Kov et al—Hypotensive effects of Geranium

Dube et al—Antibacterial effects of Geranium

Husson et al—Anti viral effects of Geranium

Yaoxuo Xubao—Anti Tumor effect of Pelargonium Greveolens

Weischer et al—Treat Diabetes by R-Alpha Lipoic acid in mammal animals

However, no prior art exists or suggests the use of Linalool alone or with other ingredients as a hypoglycemic element. In this respect, our findings are unique and establish the novelty and much more effective benefits obtainable by this invention in dealing with Diabetes Mellitus.

OBJECTS OF THE INVENTION

It is among the objects of this invention to provide a method for treating and lowering the hyperglycemia of diabetic patients.

It is another object of this invention to lower the HbAlc readings to normal levels. To enable the body to deal and control the complications of Diabetes Mellitus.

To cure diabetic patients from this disease by lowering blood sugar to normal levels permanently.

To prevent the onslaught of Diabetes Mellitus in vulnerable patients, with family history of the disease.

DETAILS OF THE INVENTION

In arriving to the conclusive results, indicated, many experiments were conducted, including:

Animal Studies

Limited clinical studies

Animal Studies

The following study was carried out and controlled by Pharmacy College, Jordan University.

1. LD 50: For this determination, 59 rats (Rattus rattus) of both sexes were used with body weights of 200–240 grams to determine the LD50. The rats were divided into groups consisting of 5–6 rats each.

The rats were fed standard laboratory pellet diet and water ad libitum. Linalool was given as one single dose subcutaneously to rats in gradually increasing doses of 0.2 ml/kg body weight, 0.25 ml/hgkg, 0.3 ml/kg, 0.35 ml/kg, 0.40 ml/kg, 0.45 ml/kg, 0.50 ml/kg, 0.55 ml/kg, 0.60 ml/kg, 0.65 ml/kg.

LD 50 was determined to be 0.63 ml/kg body weight.

2. Hypoglycemic studies of Linalool effect on Normal and Diabetic rats:

Preparation of Animals: For each experiment, eight (8) overnight fasted normoglycemic and diabetic rats were used. The animals were kept in the experimental animal laboratory for three days with free access to food and water.

Hyperglycemia was induced in the diabetic group of rats by a single intraperitoneal injection of Streptozocin (Upjohn Co, Kalamazoo, Mich., USA). 6 mg/kg body weight— freshly dissolved in citrate phosphate buffer with pH adjusted to 4.5.

Diabetes was confirmed one week after administration of Streptozocin by determining the fasting blood glucose concentration. Most of the rats exhibited blood glucose concentration in the range of 400–500 mg/dl. The fasting blood glucose concentration in normal rats is 90–120 mg/dl.

On the day of the experiment, blood samples were collected at zero time before IP injection of the test substance (Riedel De Hein—Germany), and at intervals as given in Table 1 and 2. Blood samples were drawn from the ear vein in 100 micro millimeter heparinized capillary tubes.

Blood glucose concentrations were determined according to glucose oxidase method, using glucose enzymatic kits (Biomerioux France).

The percentage change in glycaemia was calculated.

For control animals, sterile saline solution was used instead of Linalool.

Statistical Analysis

Data are expressed as means and standard error of the mean (S.E.M.) statistical analysis were performed using student's t test. The values were considered to be significantly different when P-value was less than 0.05.

Our results show that Linalool (Tables #1 and #2) has significant hypoglycemic activity in normoglycemic and hyperglycemic rats. For these normoglycemic rats, the highest activity was observed at four hours after the intraperitoneal injection of Linalool. For hyperglycemic rats the highest activity was observed at 24 hours after the Linalool injection.

TABLE 1

Short term hypoglycemic effect of a single intraperitoneal injection of Linalool (0.2 ml/kg) on blood glucose concentration of normal and Streptozocin diabetic rats

| | Pretreatment glucose (mg/100 ml) | Change in blood glucose % at | |
| --- | --- | --- | --- |
| | | 15 min. | 1 h. |
| Normoglycemic rats: | | | |
| Saline | 108 ± 10.2 | 3.2 ± 1.7 | 1.4 ± 0.6 |
| Linalool | 116.5 ± 8.7 | −36.1 ± 7.7* | −35.2 ± 6.2* |
| Hyperglycemic rats: | | | |
| Saline | 519 ± 58.8 | 2.1 ± 0.5 | −2.4 ± 0.8 |
| Linalool | 443.6 ± 28.9 | −32.1 ± 3.6* | −35 ± 3.4* |

*Significant to pretreatment values at P < 0.05
Tabular values represent the mean S.E.M.

TABLE 2

Effect of a single intraperitoneal injection of Linalool (glucose 0.2 ml/kg) on blood concentration of normal Streptozocin diabetic rats within 24 hours

| | Pretreatment glucose (mg/100 ml) | Change in blood glucose % at | | |
| --- | --- | --- | --- | --- |
| | | 1 h. | 4 h. | 24 h. |
| Normoglycemic rats: | | | | |
| Saline | 99.3 ± 4.6 | 2.0 ± 0.6 | 2.9 ± 1 | 5.4 ± 2.5 |
| Linalool | 122 ± 2.2 | −35.2 ± 6.2* | −40.9 ± 8.2* | −18.9 ± 4.4* |

TABLE 2-continued

Effect of a single intraperitoneal injection of Linalool (glucose 0.2 ml/kg) on blood concentration of normal Streptozocin diabetic rats within 24 hours

| | Pretreatment glucose (mg/100 ml) | Change in blood glucose % at | | |
| --- | --- | --- | --- | --- |
| Hyperglycemic rats: | | | | |
| Saline | 437 ± 22.4 | 5.3 ± 1.1 | 4.02 ± 2.3 | −1.1 ± 0.9 |
| Linalool | 478 ± 31.9 | −36.4 ± 8.6* | −43.7 ± 6.6* | −55.8 ± 6.2* |

*Significant to pretreatment values at P < 0.05
Tabular values represent the mean S.E.M.

There was no remarkable difference in the hypoglycemic activity in the first hour between the normo and hyperglycemic rats. This hypoglycemic activity within the first four hours after the administration of Linalool, (33.2% and 36.4%) was compared to the hypoglycemic activity of a short acting soluble insulin preparation. When 5 units of insulin were injected IP the decrease in blood glucose concentration was after one hour by the normoglycemic rats 49% and by the hyperglycemic rats 47.1%. As expected, the decrease in blood glucose concentration upon insulin injection was insignificant within the first 15 min (17.1%) while this decrease was 36.1% by normoglycemic and 32.1% by hyperglycemic rats treated by Linalool.

Results

These observations indicate that Linalool has a rapid acting and long lasting hypoglycemic activity. (Table 1 and 2).

DETAILS OF THE INVENTION

The invention is a method of administering of Linalool, alone, or Linalool with vitamin E, to treat Diabetes Mellitus.

Linalool, whose empirical formulae is (3,7 dimethyl-1,6-octadien-3-ol) can be obtained naturally or synthetically while maintaining the same level of effectiveness towards treating and preventing Diabetes Mellitus.

Linalool is also recognized by the FDA as safe, and approved flavoring substance suitable for human consumption. The method consists of administering Linalool in many forms but preferably in enteric coated softgels containing a therapeutically effective amount of Linalool oil, and vitamin E, mixed together or separately.

Daily dosages of Linalool can range from 0.20 ml, to 3 ml/day, divided in three equal doses. Vitamin E, in all its forms, alpha tocopherols beta, gamma, and delta tocopherols can be used in the product. Vitamin E is an effective antioxidant element. It is a cell protector against per oxidation of the cells of the body including beta cells of the pancreas that help maintain good function of the body cells. The outcome of this process is maintaining good function of body cells.

Dosages of vitamin E range from 0.5 mg to 20 mg/kg body weight per day in three divided doses.

The method of the invention employs the use administering of the product in the following forms:

Injectable form.

Suspension—drops, tablets, capsules.

Suppositories

Local topical applications

Stabilizers and anti-oxidants can be added to the preparation.

In the preferred embodiment of the method of the invention, a therapeutically effective amount of Linalool alone or with vitamin E, is filled into softgel enteric coated capsules. The capsules are made by a process that involves filtration of the oil, then filling the oil into softgel capsules of the selected size, with or without adding preservatives, adding anti oxidants, and then coating the ingredients by employing a reliable enteric coating method. Then packaging into hygienic packs with protection against humidity. The packaging marked with the manufacturing and expiration dates.

In the preferred embodiment of the method of the invention, the softgel enteric coated capsules contain each:

Linalool 0.5 ml,

Vitamin E 100 mg

Dosage of the preferred embodiment is 1 to 3 capsules per day taken with meals.

Duration of treatment in the preferred embodiment is three to six months.

Limited Clinical Study

The study was conducted with strict and continuous monitoring of all vital physical parameters of all volunteers. No clinical or biochemical side effects were observed during or after the test periods. Special attention was made while monitoring Blood Urea, Serum Creatinine, SGPT, Cholesterol, and Triglycerides.

The study involved over 200 diabetic volunteers with different types of Diabetes Mellitus and from different countries, and of both sexes. The breakdown was as follows:

Group One: Two (2) volunteers were new Diabetes Mellitus patients (Virgin cases).

These volunteers had never been treated for the disease and never taken any of the known and standard Diabetes Mellitus medications.

Volunteer from (Group One)—Mr. A. M. Shanawani, Male, 45 years old, (Jordan citizen). First determined to be diabetic on Jan. 21st, 1999. Readings with no previous medications, or treatments were as follows:

| February 2nd, 1999 | Serum Glucose, Fasting | 184 mg/dl |
| --- | --- | --- |
| | HbAlc | 9.0% |
| | Insulin, Fasting | 10 uU/mL |
| | Serum Glucose PP | 343 mg/dL |
| | Insulin PP | 37.20 uU/mL |

Started using Linalool Enteric Coated Softgels 0.45 ml 3 times daily with meals, on Feb. 22nd, 1999.

| April 13th, 1999 | Serum Glucose, Fasting | 120 mg/dL |
| --- | --- | --- |
| | HbAlc | 8.00% |
| | Insulin, Fasting | 10.70 uU/mL |
| | Serum Glucose PP | 257 mg/dL |
| | Insulin PP | 57.01 uU/mL |

-continued

| May 25th, 1999 | Serum Glucose, Fasting | 125 mg/dL |
| --- | --- | --- |
| | HbAlc | 6.70% |
| | Insulin, Fasting | 7.30 uU/mL |
| | Serum Glucose PP | 244 mg/dL |
| | Insulin PP | 59.10 uU/mL |
| July 18th, 1999 | Serum Glucose, Fasting | 136 mg/dL |
| | HbAlc | 6.40% |
| | Insulin, Fasting | 5.90 uU/mL |
| | Serum Glucose PP | 244 mg/dL |
| | Insulin PP | 72.80 uU/mL |

Interpretation of Results

Above volunteer enjoyed drastic improvement in hyperglycemia, because of the Linalool method of treatment, due to activation of the beta cells, and therefore their ability to secrete insulin. Since no insulin injections were given to this volunteer, the increase in his insulin levels PP is attributed to the Linalool Treatment Method only. The results prove that this method of treatment enabled the pancreas to perform in a normal manner by increasing the output and production of insulin when needed at the PP stage.

Group Two: One (1) volunteer had hyper insulinemia with readings of 400 mg/dl of glucose 2—Volunteer Mr. Omar Bakir—Male, Age 55 years (Jordan citizen).

Diagnosed to be diabetic on Feb. 28th, 1997

Readings with no previous medications, or treatments were on Mar. 29, 1997 as follows:

| February 2nd, 1999 | Serum Glucose, Fasting | 197 mg/dl |
| --- | --- | --- |
| | HbAlc | 8.2% |
| | Insulin, Fasting | 42 uU/mL |
| May 17th, 1999 | Serum Glucose, Fasting | 200 mg/dl |
| | HbAlc | 8.1% |
| | Insulin, Fasting | 18.40 uU/mL |
| June 24th, 1 999 | Serum Glucose, Fasting | 222 mg/dl |
| | HbAlc | 7.5% |
| | Insulin, Fasting | 25.6 uU/mL |

Interpretation of Results

Above volunteer had high level of fasting insulin, 42 uU/mL but was still suffering from diabetes, thus he had hyper insulinemia. His HbAlc reading was lowered to 7.5% while insulin level decreased to 25.6, almost a 50% reduction. This means that Linalool caused improvement in utilizing glucose, due to activation of insulin receptors in peripheral cells.

Comments on Group One and Two

From above two volunteers, it is established that the product of the method of the invention method has two actions:

Increased production and secretion of insulin by the pancreas.

Activation of the insulin receptors of the cells increasing the glucose utilization by the body.

Group Three

The study involved over two hundred diabetic volunteers of both sexes, who had the disease from 3 to 25 years. In various lots, the volunteers were on insulin alone, insulin and hypoglycemic drugs, or hypoglycemic drugs alone. The patients took the product in the form of softgel enteric coated capsules (0.5 ml Linalool and 100 mg vitamin E) one capsule with meals three times a day. The duration of treatment was minimum three months. The product was given along with the classical hypoglycemic treatment (insulin and others). These classical hypoglycemic medications, Insulin-morning and evening, and Daonil (Glibenclamide 5 mg), Glucaphage (metformin 850 mg and other medications, were decreased gradually depending on the monitored improvements of the patient condition.

Results of the Group Three Study

HbA1c was lowered to normal levels in all patients.

The fasting blood sugar was lowered to normal levels.

In three cases, complete cure was accomplished, with no further anti diabetic drugs taken.

Select examples of volunteers from Group Three: (Summary of readings):

3—Mr. L. W. 50 years, USA citizen.

| Blood test, Glucose Fasting October 15, 1998 | 333 mg/dL |
| Blood test, Glucose Fasting November 9, 1998 | 285 mg/dL |
| May 25th | 153 |
| June 1st | 153 |

HbAlC Readings:

| October 15th, 1998 | HbAlc | 9.0% |
| January 4th, 1999 | HbAlc | 8.1% |
| April 7th, 1999 | HbAlc | 6.9% |

4—Mr. T. B., 68 years old, USA Citizen, semi retired from serving as a high ranking executive in the railroad industry and the State government. He has been treated regularly by the Linalool method, and enjoyed regular and continuous improvements in his condition.

He writes on Jul. 7th, 1999 "after reviewing my report last month, my physician reduced my medication to one half. He indicated that if my readings continued to be low, he would take me off all medication".

On July 14th, his physician decided to take him off all medication, and considered him CURED. Below, is history of his readings:

| Dec. 17th | 175 mg/dL |
| Dec. 24th | 163 |
| June 18th | 109 |
| June 26th | 105 |
| July 26th, 99 | 105 mg/dL |

HbAlc Readings: Were lowered from 9.3% to 6.18% on June 4$^{th}$, 1999.

5—Mr. Y. A., 52 years old, Jordan citizen, diabetic for over 20 years. His best HbAlc reading occurred on Jan. 27th, 1999 and was 7.0%, down from a high of 11.2% on Jul. 27th, 1998.

It is also worth noting that this volunteer, a leading financier and president of a well known Middle Eastern bank, who regularly undergoes general physical tests in the USA, has been treated with the method of the invention for over three years, in various embodiments of the method, including injections and orally. Despite his disregard for dietary caution, the volunteer continued to eat large amounts of sweets and fat rich foods, yet benefited tremendously, with no ill effects or negative signs in his general health. He confirms his belief that his health is continuously improving and attributes that to the Linalool method. He says, "As far as knowing my general health and diabetic condition are concerned, I am as good as any of my doctors."

| READINGS | | |
|---|---|---|
| | Fasting Blood Sugar | HbAlc |
| July 27th, 1998 | 233 mg/dL | 11.2% |
| August 17th, 1998 | 190 | 10.1% |
| September 17th, 1998 | 166 | 9.7% |
| November 1st, 1998 | 114 | |
| November 12th, 1998 | 135 | 7.5% |
| January 27th, 1999 | 167 | 7.0% |

What is claimed is:

1. A method for treating hyperglycemia comprising administering orally, topically or rectally a therapeutically effective amount of Linalool and vitamin E to a human patient in need thereof.

2. The method of claim 1, wherein the patient has Diabetes Mellitus.

3. The method of claim 1, wherein the Linalool is administered in a suppository.

4. The method of claim 1, wherein the Linalool is administered orally.

5. The method of claim 1, wherein the Linalool is administered orally in enteric coated softgels.

6. The method of claim 1, wherein said Linalool is administered in a dosage of from about 0.2 to about 3.0 ml/day.

7. The method of claim 1, wherein the vitamin E is administered mixed together with said Linalool.

8. A method for treating hyperglycemia comprising administering a therapeutically effective amount of Linalool and at least one hypoglycemic agent to a human patient in need thereof.

9. The method of claim 8, wherein the Linalool is administered orally, topically, rectally.

10. The method of claim 8, wherein the Linalool is administered in a suppository.

11. The method of claim 8, wherein the Linalool is administered orally.

12. The method of claim 8, wherein the Linalool is administered orally in enteric coated softgels.

13. The method of claim 8, wherein the vitamin E is administered mixed together with said Linalool.

14. The method of claim 8, wherein said Linalool is administered in a dosage of from about 0.2 to about 3.0 ml/day.

* * * * *